US006572604B1

(12) United States Patent
Platt et al.

(10) Patent No.: US 6,572,604 B1
(45) Date of Patent: Jun. 3, 2003

(54) OCCLUSION DETECTION METHOD AND SYSTEM FOR AMBULATORY DRUG INFUSION PUMP

(75) Inventors: Michael Platt, Mt. Prospect, IL (US); Ralph LaBedz, McHenry, IL (US); Patrick Hovis, Rockford, IL (US); Ronald P. Spang, Racine, WI (US)

(73) Assignee: Baxter International Inc., Deerfield, IL (US)

( * ) Notice: Subject to any disclaimer, the term of this patent is extended or adjusted under 35 U.S.C. 154(b) by 161 days.

(21) Appl. No.: 09/708,112

(22) Filed: Nov. 7, 2000

(51) Int. Cl.⁷ .............................................. A61M 31/00
(52) U.S. Cl. ...................................................... 604/500
(58) Field of Search ..................... 604/500, 48, 290, 604/358, 501, 892.1, 540; 600/407

(56) References Cited

U.S. PATENT DOCUMENTS

| | | | |
|---|---|---|---|
| 4,469,480 A | * | 9/1984 | Figler |
| 4,882,575 A | | 11/1989 | Kawahara |
| 5,116,203 A | | 5/1992 | Natwick et al. |
| 5,254,096 A | | 10/1993 | Rondelet et al. |
| 5,389,071 A | * | 2/1995 | Kawahara |
| 5,647,853 A | | 7/1997 | Feldmann et al. |
| 5,695,473 A | | 12/1997 | Olsen |
| 5,720,721 A | * | 2/1998 | Dumas |
| 5,906,589 A | | 5/1999 | Gordon et al. |
| 5,935,099 A | | 8/1999 | Peterson et al. |
| 5,935,106 A | | 8/1999 | Olsen |
| 5,951,510 A | | 9/1999 | Barak |
| 6,231,560 B1 | * | 5/2001 | Bui |

FOREIGN PATENT DOCUMENTS

EP    0 315 312 A1    10/1989

OTHER PUBLICATIONS

International Search Report for International Application No. PCT/US 01/45621 of Applicant Baxter International Inc.

* cited by examiner

Primary Examiner—Teresa Walberg
Assistant Examiner—Daniel Robinson
(74) Attorney, Agent, or Firm—Wallenstein & Wagner

(57) ABSTRACT

A method of detecting an occlusion within a flexible infusion tube by measuring samples indicative of pressures relative to instances in time. Difference values for the samples are created. The difference values are compared to percentages of other difference values. When appropriate, an occlusion signal is generated in response to a comparison of a difference value to a percentage of another difference value.

21 Claims, 1 Drawing Sheet

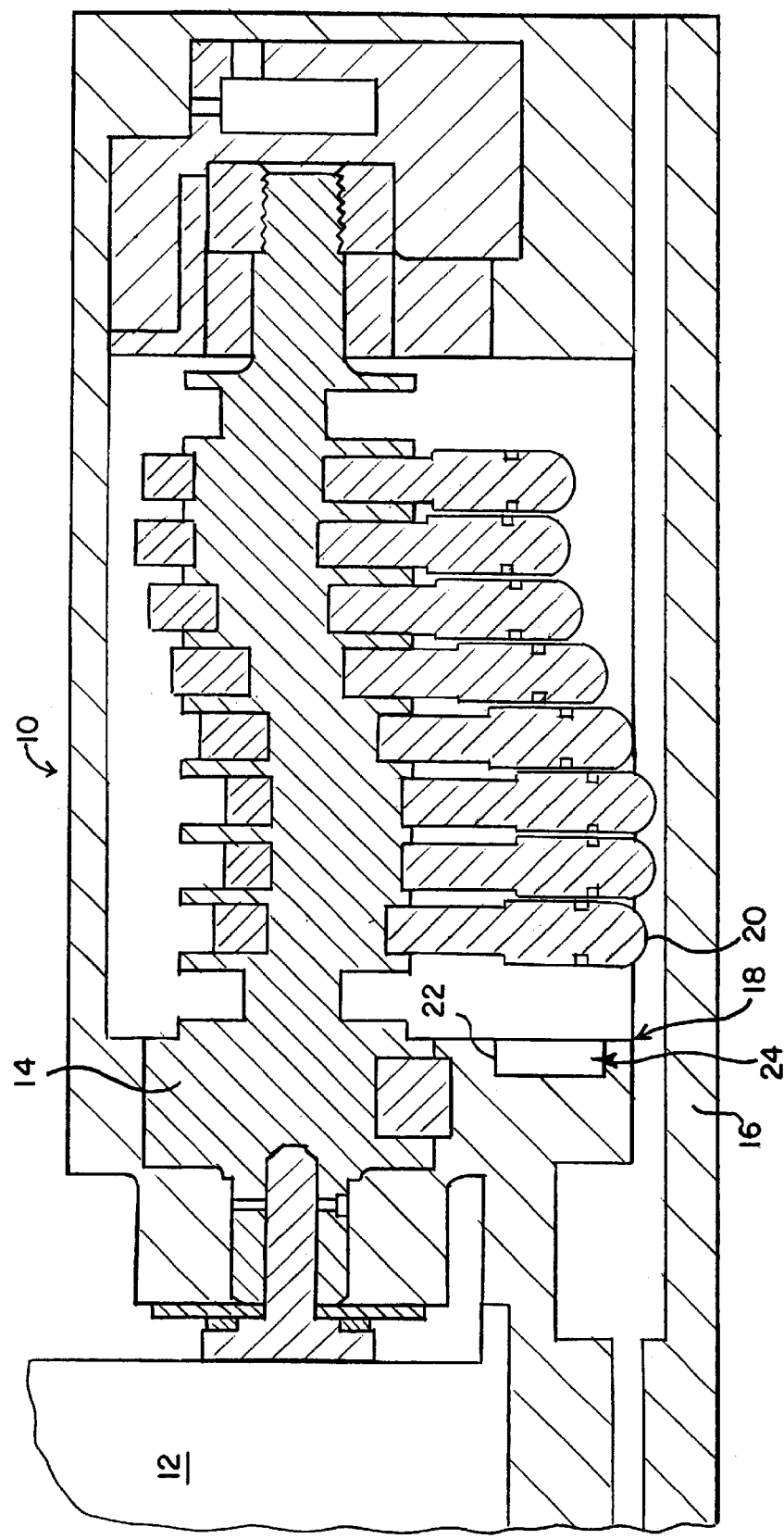

OCCLUSION DETECTION METHOD AND SYSTEM FOR AMBULATORY DRUG INFUSION PUMP

DESCRIPTION

1. Technical Field

The invention relates generally to monitoring fluid flow, and more particularly, to detecting upstream fluid occlusions in an intravenous fluid administration system.

2. Background of the Invention

Fluid delivery systems for infusing parenteral fluids are commonly used in hospitals and typically include an inverted bottle or bag or other means of supply of parenteral fluid, an intravenous (IV) administration set and an infusion pump for controlled delivery to a vascular system of a patient. The fluid administration set typically includes a flexible infusion tube, a drip chamber, injection sites among other components, and a catheter mounted to the distal end of the flexible infusion tube adapted to be inserted into the patient's blood vessel. Commonly, the pump is of a peristaltic type in which a plurality of fingers, rollers, or other devices sequentially constrict the tubing along a moving region of occlusion to move fluid through the tubing.

One of the difficulties of infusion systems is the evaluation of the condition of the fluid flow upstream of the pump. Where an occlusion of the infusion tube exists upstream of the pump, the pump will not succeed in infusing the parenteral fluid to the patient even though the pump may continue to operate. Similarly, when the parenteral fluid supply becomes depleted, the pump may also continue to operate, however no parenteral fluid will be administered to the patient.

One previous method for detecting a decrease in the fluid supply or an upstream occlusion was visual observation of a drip chamber. However, visually verifying the existence of drops places an undesirable burden on the hospital staff.

In infusion systems utilizing peristaltic pumps, detection of upstream occlusions has been accomplished through the use of an opto-electric drop detector combined with a drip chamber. The opto-electric drop detector detects upstream occlusions, such as occlusions caused by a clamp or kink in the upstream tubing, by detecting an absence of drops. However, the opto-electric drop detector has several disadvantages. Significant movement of the IV administration set can cause a surplus of drops to fall from the drop former or can interrupt the drop formation, thereby causing inaccurate drop counts and false alarms. Ambient light can also interfere with the accuracy of an optical drop sensor.

Another method for detecting upstream occlusions is to incorporate a pressure sensor into the pumping mechanism of the infusion pump. In one such device, a pressure transducer is placed in the middle of the pumping area, allowing direct measurement of the pressure in the pump segment of the fluid tube. The resulting measurement is indicative of the inlet pressure. However, this method can adversely affect flow uniformity and may require substantial modifications to the pumping mechanism.

Pump systems have been disclosed that include a downstream pressure sensor used for detecting improper fluid communication with the patient. Such systems include U.S. Pat. No. 4,743,228 to Butterfield; U.S. Pat. No. 4,460,355 to Layman; U.S. Pat. No. 4,534,756 to Nelson; and U.S. Pat. No. 5,356,378 to Doan.

In operation, peristaltic pump mechanisms sequentially occlude the pumping segment of the tube, also known as the pumping control segment, to alternately expose the pumping segment to fluid communication with the upstream and downstream portions of the infusion tube. The pumping segment is at upstream pressure when exposed to the upstream portion of the fluid line. When the pumping segment is subsequently exposed to the downstream portion, the fluid within the pumping segment, which was at upstream pressure, causes a change in pressure, i.e., a pressure difference, as the pumping segment pressure equalizes with the downstream portion.

There have been pump systems with downstream pressure sensors that have utilized analysis of such pressure differences to detect upstream occlusions. If a large negative pressure difference occurs, an upstream occlusion is presumed. However, pumping into high downstream pressures can create pressure waveform conditions, including drops in pressure, that mimic the appearance of true upstream occlusions. Additionally, pressure sensors may exhibit substantial offset errors that can also mimic upstream occlusion conditions. Pressure sensors used with infusion systems may express variance in their readings that can deviate substantially from the desired values. Such variances, which may be produced by temperature differences or other factors such as the composition of the infusion tube, can cause false alarms. These false alarms detract from the usefulness of an occlusion detection system. While in some cases these variances may be reduced through compensation circuits or closer tolerances on various mechanical and circuit elements, these approaches may substantially complicate the device.

Accordingly, it is desirable to use an upstream pressure sensor having accuracy requirements less stringent than absolute values or threshold values while avoiding false alarms.

Hence, those skilled in the art have recognized the need for a infusion tube monitoring system that can automatically detect upstream infusion tube occlusions while minimizing false alarms. Additionally, those skilled in the art have recognized a need to reduce the cost of a system capable of determining such upstream infusion tube conditions. The present invention fulfills these needs and others.

SUMMARY OF THE INVENTION

Other advantages and aspects of the present invention will become apparent upon reading the following description of the drawings and detailed description of the invention.

Accordingly, the present invention provides a method and system for the detection of upstream occlusions in flexible infusion tubing so as to allow for the minimization of false occlusion alarms. The method is used within an occlusion detection system. The occlusion detection system for detecting occlusions inhibiting a fluid flowing in a tube adapted for connection to a fluid pump has a pressure sensor for releasable attachment to the tube upstream of the fluid pump for monitoring a negative pressure condition. The occlusion detection system contains a transducer operably attached to the pressure sensor, the transducer converts the monitored negative pressure condition in a fluid tube into a usable signal. The occlusion detection system further includes an alarm module that is responsive to a signal indicating that the negative pressure condition is outside an acceptable range.

In one aspect of the present invention, the transducer is attached to the pressure sensor that makes contact with the flexible infusion tube. Several types of transducers may be used with the occlusion detection system. These include, but are not limited to, a force sensing resistor, a piezoresistive sensor, a piezoelectric sensor, a diaphragm piston gauge, a bending beam gauge, a strain gauge, a hall-effect sensor, a ¼ bridge strain gauge, a ½ bridge strain gauge, or a full bridge strain gauge. In another aspect of the present invention, the fluid pump may be selected from the group consisting of a peristaltic pump, a roller pump, an expulsor pump, a finger pump and a piston cassette pump. In yet another aspect of the present invention, the pressure sensor can be calibrated with a calibration gauge. In some applications, the signaling of an upstream occlusion may be over a network.

In addition to the above, the method of detecting an occlusion within a flexible infusion tube includes the steps of measuring a first sample indicating a pressure in the tube relative to a first instance in time; measuring a second sample indicating a pressure in the tube relative to a second instance in time; measuring a third sample indicating a pressure in the tube relative to a third instance in time; creating a first difference value of the first sample to the second sample; creating a second difference value of the second sample to the third sample; comparing the first difference value to a percentage of the second difference value; and generating an occlusion signal in response to the step of comparing the first difference value to the second difference value.

In yet another aspect of the present invention, the method of detecting an occlusion within a flexible infusion tube includes the steps of measuring a first sample indicating a pressure in the tube relative to a first instance in time; measuring a second sample indicating a pressure in the tube relative to a second instance in time; creating a first difference value of the first sample to a second sample; comparing the first difference value to a percentage of a second difference value; and generating an occlusion signal in response to the step of comparing the first difference value to a second difference value.

In another aspect of the present invention, the system for detecting an occlusion within a flexible infusion tube includes a measuring device for measuring a first sample indicating a pressure in the tube relative to a first instance in time; the measuring device also measuring a second sample indicating a pressure in the tube relative to a second instance in time; the measuring device also measuring a third sample indicating a pressure in the tube relative to a third instance in time; the measuring device also creating a first difference value of the first sample to the second sample; the measuring device also creating a second difference value of the second sample to the third sample; the measuring device also comparing the first difference value to a percentage of the second difference value; and an alarm module generating an occlusion signal in response to the measuring device also comparing the first difference value to the second difference value.

In yet another aspect of the present invention, the system for detecting an occlusion within a flexible infusion tube includes a measuring device for measuring a first sample indicating a pressure in the tube relative to a first instance in time; the measuring device also measuring a second sample indicating a pressure in the tube relative to a second instance in time; the measuring device also creating a first difference value of the first sample to a second sample; the measuring device also comparing the first difference value to a percentage of a second difference value; and an alarm module generating an occlusion signal in response to the measuring device also comparing the first difference value to the second difference value.

BRIEF DESCRIPTION OF THE DRAWINGS

The above and other objects, features, and advantages of the present invention will become apparent from a consideration of the subsequent detailed description presented in connection with the accompanying drawing, in which:

FIG. 1 is a cross-sectional view of a pump containing the upstream occlusion system.

DETAILED DESCRIPTION OF THE PREFERRED EMBODIMENT

While this invention is susceptible of embodiments in many different forms, there is shown in the drawings and will herein be described in detail a preferred embodiment of the invention. The present disclosure is to be considered as an exemplification of the principles of the invention and is not intended to limit the broad aspect of the invention to the embodiment illustrated.

Referring now to FIG. 1, a pump 10 is shown which includes a motor 12, a camshaft 14, a tubing set 16, and an upstream occlusion system 18.

The motor 12 is operably connected to and facilitates the movement of the camshaft 14.

Camshaft 14 accommodates a plurality of pumping fingers 20. The pumping fingers 20 facilitate the pumping action that maintains the fluid flow. The pumping action results from the motor 12 engaging the camshaft 14, the motor 12 then imparting rotational movement to the camshaft 14. Once the camshaft 14 is in rotational movement, the pumping fingers 20 sequentially apply waveform pressure on the tubing set 16.

The tubing set 16 preferably consists of a flexible infusion tube. The tubing set 16 originates from the fluid supply, preferably an intravenous solution bag. The tubing set 16 enters pump 10 and passes through the upstream occlusion system 18. The tubing set 16 passes through the upstream occlusion system 18 prior to having waveform pressure applied by the pumping fingers 20.

The upstream occlusion system 18 is composed of a pressure sensor 22 for releasable attachment to the tubing set 16 upstream of the pumping fingers 20, a transducer 24 operably attached to the pressure sensor 22, and an alarm module 26 for signaling that the occlusion has occurred in response to the alarm module 26 receiving the useable signal from the transducer 24.

The pressure sensor 22 is for monitoring a negative pressure condition. In a preferred embodiment, the pressure sensor 22 is releasably attached to the tubing set 16 upstream of the pump 10.

The transducer 24, operably attached to pressure sensor 22, preferably converts the monitored negative pressure condition in the tubing set 16 into a usable signal. The transducer 24 may be a force sensing resistor, a piezoresistive sensor, a piezoelectric sensor, a diaphragm piston gauge, a bending beam gauge, a strain gauge, a hall-effect sensor, a ¼ bridge strain gauge, a ½ bridge strain gauge, or a full bridge strain gauge.

The alarm module 26 generates a signal indicating that the negative pressure condition is outside an acceptable range.

The first step in detecting an occlusion in a tubing set is obtaining the initial voltage of the tubing set at the start of a pumping cycle. Preferably, detecting an occlusion in tubing set 16 at the start of the pumping cycle of pump 10 begins where the pressure sensor 22 measures the initial voltage of the tubing set 16. The initial voltage is the voltage at the start-up of pump 10. The pressure sensor 22 then measures both the high voltage of the tubing set 16 for the first pumping cycle of pump 10 and the low voltage of the tubing set 16 for the first pumping cycle of pump 10.

The transducer 24 converts these voltage readings into signals usable for the pump 10 in determining the presence of an upstream occlusion. The presence of an upstream occlusion at pump start-up is determined by where the initial voltage at pump start-up falls in a particular range of values. The range of values is composed of percentages of the high voltage determined for the first pumping cycle.

The pump 10 is calibrated without calibration software, only requiring a calibration gauge. The calibration gauge simulates an upstream occlusion. A potentiometer is used to set the upstream occlusion system's output to the proper limits of the operating range.

In one example, if the initial voltage at pump start-up is within 10% of the high voltage value for the first pumping cycle, i.e., where the difference between the initial voltage and the low voltage for the first pumping cycle is less than 10% of the difference between the high voltage and the low voltage for the first pumping cycle, then the pump 10 generates an occlusion signal if a high voltage value of a subsequent pumping cycle subtracted from the high voltage value of a first pumping cycle is greater than about 40 percent of the high voltage value of a first pumping cycle minus the initial low voltage value of a first pumping cycle.

In another example, if the initial voltage at pump start-up is within 50% of the low voltage value for the first pumping cycle, i.e., where the difference between the initial voltage and the low voltage for the first pumping cycle is less than 50% of the difference between the high voltage and the low voltage for the first pumping cycle, then the pump 10 generates an occlusion signal if a high voltage value of a subsequent pumping cycle subtracted from the initial high voltage value of a first pumping cycle is greater than about 20 percent of the initial high voltage value of a first pumping cycle minus the initial low voltage value of a first pumping cycle.

In yet another example, if the initial voltage at pump start-up does not fall within a prescribed range for the first pumping cycle, then the pump 10 generates an occlusion signal if a high voltage value of a subsequent pumping cycle subtracted from the initial high voltage value of a first pumping cycle is greater than about 30 percent of the initial high voltage value of a first pumping cycle minus the initial low voltage value of a first pumping cycle.

In still another example, once pump 10 has completed a predetermined number of cycles, the pump 10 will generate an occlusion signal if the difference of the initial high voltage value of a first pumping cycle and a high voltage value of a subsequent pumping cycle is greater than about 25 percent of the initial high voltage value of a first pumping cycle minus the initial low voltage value of a first pumping cycle.

In a further example, in order to avoid false occlusion alarm signals as the contents of the fluid bag of administration system are depleted, the pump 10 will generate an occlusion signal if after completing a predetermined number of cycles the difference of the initial high voltage value of a first pumping cycle and the high voltage values of at least about every eighth pumping cycle is greater than about 15 percent of the initial high voltage value of a first pumping cycle minus the initial low voltage value of a first pumping cycle.

Preferably, if an occlusion signal is generated, the pump 10 discontinues the pumping cycle. Once the pumping cycle is discontinued, the pump 10 must be reset manually. Upon restart, the pump 10 will, for example, generate an occlusion signal if the difference of the initial high voltage value prior to occlusion minus the initial high voltage value of the first pumping cycle after occlusion is greater than a percentage of the initial high voltage value of a first pumping cycle prior to occlusion minus the initial low voltage value of a first pumping cycle prior to occlusion.

In view of the foregoing, it can be appreciated that the present invention provides a simple, low cost apparatus and method for detecting upstream occlusions in the tubing set of an IV fluid administration system without the necessity of modifying existing pump mechanisms. Although preferred and alternative embodiments of the invention have been described and illustrated, the invention is susceptible to modifications and adaptations within the ability of those skilled in the art and without the exercise of inventive faculty. Thus, it should be understood that various changes in form, detail and usage of the present invention may be made without departing from the spirit and scope of the invention.

We claim:

1. A method of detecting an occlusion within a flexible infusion tube, comprising the steps of:

measuring a first sample indicating a pressure in the tube relative to a first instance in time;

measuring a second sample indicating a pressure in the tube relative to a second instance in time;

creating a first difference value of the first sample to a second sample;

comparing the first difference value to a percentage of a second difference value; and generating an occlusion signal in response to the step of comparing the first difference value to a second difference value.

2. The method of claim 1 wherein the occlusion signal is generated when the first difference value is greater than a percentage of a second difference value.

3. The method of claim 2 wherein the first sample is a first voltage level, and wherein the second sample is a second voltage level.

4. The method of claim 3 wherein the measuring further comprises:

measuring a high sample for the pumping cycle; and measuring a low sample for the pumping cycle.

5. The method of claim 4 wherein each measured sample is recorded.

6. The method of claim 5 wherein the start sample is a start voltage level, wherein the high sample is a high voltage level, and wherein the low sample is a low voltage level.

7. The method of claim 6 wherein the occlusion value is selected from a group consisting of a high voltage difference value equation, a low voltage difference value equation, a median voltage difference value equation, a steady state difference value equation, an end of bag difference value equation, and a restart difference value equation.

8. The method of claim 7 wherein the high voltage difference value equation determines occlusion presence where a high voltage value of a subsequent pumping cycle subtracted from the initial high voltage value of a first pumping cycle is greater than about 40 percent of the initial high voltage value of a first pumping cycle minus the initial low voltage value of a first pumping cycle.

9. The method of claim 8 wherein the low voltage difference value equation determines occlusion presence where a high voltage value of a subsequent pumping cycle subtracted from the initial high voltage value of a first pumping cycle is greater than about 20 percent of the initial high voltage value of a first pumping cycle minus the initial low voltage value of a first pumping cycle.

10. The method of claim 9 wherein the median voltage difference value equation determines occlusion presence where a high voltage value of a subsequent pumping cycle subtracted from the initial high voltage value of a first pumping cycle is greater than about 30 percent of the initial high voltage value of a first pumping cycle minus the initial low voltage value of a first pumping cycle.

11. The method of claim 10 wherein the steady state difference value equation determines occlusion presence where the difference of the initial high voltage value of a first pumping cycle and a high voltage value of a subsequent pumping cycle are greater than about 25 percent of the initial high voltage value of a first pumping cycle minus the initial low voltage value of a first pumping cycle.

12. The method of claim 11 wherein the steady state difference value equation determines occlusion presence may be used to determine occlusion for multiple pumping cycles after:

a high voltage difference value equation;

a low voltage difference value equation; or a median voltage difference value equation.

13. The method of claim 12 wherein the end of bag difference value equation determines occlusion presence where the difference of the initial high voltage value of a first pumping cycle and the high voltage values of at least about every eighth pumping cycle is greater than about 15 percent of the initial high voltage value of a first pumping cycle minus the initial low voltage value of a first pumping cycle.

14. The method of claim 13 wherein the restart difference value equation determines occlusion presence where the difference of the initial high voltage value prior to occlusion minus the initial high voltage value of the first pumping cycle after occlusion is greater than a percentage of the initial high voltage value of a first pumping cycle prior to occlusion minus the initial low voltage value of a first pumping cycle prior to occlusion.

15. The method of claim 14 wherein the percentage of the initial high voltage value of a first pumping cycle prior to occlusion minus the initial low voltage value of a first pumping cycle prior to occlusion is from at least about 15 percent to about 40 percent.

16. The method of claim 15 wherein the percentage of the initial high voltage value of a first pumping cycle prior to occlusion minus the initial low voltage value of a first pumping cycle prior to occlusion is the percentage of the initial high voltage value of a first pumping cycle minus the initial low voltage value of a first pumping cycle for the equation that determined occlusion.

17. The method of claim 16 wherein the equations to determine an occlusion comprise a high voltage difference value equation, a low voltage difference value equation, a median voltage difference value equation, a steady state difference value equation, an end of bag difference value equation, and a restart difference value equation.

18. The method of claim 17 wherein the pumping cycle may be reset.

19. The method of claim 18 wherein the restart equation may be used after the pumping cycle is reset.

20. The method of claim 19 wherein the data is stored in electronically readable memory.

21. The method of claim 20 wherein the signal indicating an occlusion is sent over a network.

\* \* \* \* \*

UNITED STATES PATENT AND TRADEMARK OFFICE
CERTIFICATE OF CORRECTION

PATENT NO.      : 6,572,604 B1
DATED           : June 3, 2003
INVENTOR(S)     : Michael Platt et al.

It is certified that error appears in the above-identified patent and that said Letters Patent is hereby corrected as shown below:

<u>Title page,</u>
Item [75], Inventors, "Ronald P. Spang" delete the initial "P" and replace with the initial H --.

Signed and Sealed this

Twenty-eighth Day of October, 2003

JAMES E. ROGAN
*Director of the United States Patent and Trademark Office*